(12) United States Patent
Almodhen

(10) Patent No.: US 8,597,308 B2
(45) Date of Patent: Dec. 3, 2013

(54) LAPAROSCOPIC TOOL AND METHOD FOR A LAPAROSCOPIC SURGERY

(75) Inventor: Fayez Almodhen, Riyadh (SA)

(73) Assignee: Fayez Almodhen, Riyadh (SA)

(*) Notice: Subject to any disclaimer, the term of this patent is extended or adjusted under 35 U.S.C. 154(b) by 37 days.

(21) Appl. No.: 13/146,397

(22) PCT Filed: Jan. 30, 2009

(86) PCT No.: PCT/CA2009/000117
§ 371 (c)(1),
(2), (4) Date: Oct. 12, 2011

(87) PCT Pub. No.: WO2010/085869
PCT Pub. Date: Aug. 5, 2010

(65) Prior Publication Data
US 2012/0136377 A1    May 31, 2012

(51) Int. Cl.
*A61B 17/04* (2006.01)

(52) U.S. Cl.
USPC .............................. 606/144; 600/37

(58) Field of Classification Search
USPC ......... 606/139, 144, 147, 148, 151, 153, 232; 600/37, 104, 127, 129; 128/898
See application file for complete search history.

(56) References Cited

U.S. PATENT DOCUMENTS

| | | | |
|---|---|---|---|
| 5,662,654 A * | 9/1997 | Thompson | 606/232 |
| 6,197,351 B1 | 3/2001 | Neuwirth | |
| 8,147,515 B2 * | 4/2012 | Ohdaira | 606/232 |
| 2005/0055052 A1 | 3/2005 | Lombardo et al. | |
| 2005/0234512 A1 | 10/2005 | Nakao | |
| 2008/0009904 A1 | 1/2008 | Bourque et al. | |
| 2008/0114380 A1 * | 5/2008 | Takemoto et al. | 606/144 |
| 2009/0112234 A1 * | 4/2009 | Crainich et al. | 606/144 |

FOREIGN PATENT DOCUMENTS

| | | |
|---|---|---|
| CN | 1644156 A | 7/2005 |
| CN | 201094617 Y | 8/2008 |
| EP | 1557130 A1 | 7/2005 |
| JP | 11-507353 A | 6/1999 |
| WO | 2005/037112 A1 | 4/2005 |
| WO | 2008/001882 A1 | 1/2008 |

OTHER PUBLICATIONS

International Search Report and Written Opinion received for PCT Patent Application No. PCT/CA2009/000117, mailed on Oct. 19, 2009, 8 pages.

(Continued)

*Primary Examiner* — Dianne Dornbusch
*Assistant Examiner* — Robert Lynch
(74) *Attorney, Agent, or Firm* — Morrison & Foerster LLP

(57) ABSTRACT

A laparoscopic tool for surgery on an internal body tissue of a patient. The laparoscopic tool comprises a main body to which is affixed an attachment. The main body has a main aperture for fixing a compatible anchor. The attachment has a support member connected to the main body, and a needle portion connected to the support member. The needle portion has an interlocking mechanism to interlock with the support member. The attachment is deployable from a first position aligned with the main body, for insertion through a laparoscopic port, to a second position unaligned with the main body, for insertion into a tissue and for anchoring the tool to the tissue. A method of performing a laparoscopic surgery using the laparoscopic tool, the use of the laparoscopic tool for laparoscopic surgery, and kits for laparoscopic surgery comprising the laparoscopic tool and the compatible anchor are also disclosed.

19 Claims, 8 Drawing Sheets

(56) References Cited

OTHER PUBLICATIONS

International Preliminary Report on Patentability received for PCT Patent Application No. PCT/CA2009/000117, completed on Apr. 13, 2011, 6 pages.

Office Action received for Chinese Patent Application No. 200980155792.7, issued on Mar. 14, 2013, 9 pages. (4 pages of English Translation and 5 pages of Office Action).

* cited by examiner

LAPAROSCOPIC TOOL AND METHOD FOR A LAPAROSCOPIC SURGERY

CROSS REFERENCE TO RELATED APPLICATIONS

This application is a U.S. National Phase patent application of PCT/CA2009/000117, with a filing date of Jan. 30, 2009, which is incorporated herein by reference in its entirety.

FIELD OF THE INVENTION

The subject matter disclosed generally relates to a surgical tool. More precisely, the present invention generally relates to a laparoscopic tool for laparoscopic surgery on an internal body tissue of a patient to be used in conjunction with a compatible anchor to secure or retract internal body tissues during the surgery.

BACKGROUND OF THE INVENTION

During surgery, it sometimes happens that a surgeon has to reach a region to be operated upon that is located underneath an internal organ of a patient. In such cases, it is common in the art of surgery to anchor or retract the organ, or other internal soft body tissues, using suture anchor while performing the medical procedure. An approach often employed during traditional surgical procedures is by securing a suture anchor in a previously prepared borehole in a rigid structure such as an adjacent bone. A suture may then be attached to the anchor to secure the soft tissue in place. U.S. Patent Application No. 2005/055052 to Lombardo et al. describes a knotless suture anchor and method for insertion into tissue, thereby allowing one to reversibly secure soft tissue without tying a knot. U.S. Patent Application No. 2008/0009904 to Bourque et al. also describes a soft tissue fixation device that is used in the repair of soft tissue such as ligaments and tendons by insertion of the anchor into bone followed by attachment of sutures to the bone. These approaches, however, are not suitable for laparoscopic surgeries as no such adjacent rigid structure are conveniently accessible.

Laparoscopic surgery is a modern surgical technique in which operations in the abdomen are performed through small incisions (usually 0.5-1.5 cm) that are much less invasive than the larger incisions needed in traditional surgical procedures. During laparoscopic surgery, more traditional tools such as those described above may either not be used for lack of space or simply because they do not fit within a laparoscopic port. Instead, in order to fix or retract organs, laparoscopic surgeons use suture threads that are inserted at a first site, for example through an abdominal wall, looped and wound around a target organ and reinserted at the first site. The suture thread is then pulled to retract the target organ. Such an operation must be repeated multiple times for every organ in need of retracting, thereby increasing the time of the often-delicate procedures. Such a method of retracting is depicted in FIG. 1.

Laparoscopic surgery is performed through a limited number of laparoscopic ports. These ports, which are points of entry into the abdomen, have to be used efficiently during the surgical procedure. U.S. Patent Application No. 2005/0234512 to Nakao describes an endoscopic anchoring device assembly. The device comprises a series of anchor that may be delivered inside the patient and deployed into a target tissue, the device being operated by the surgeon extracorporeally through a pushing operation. However, this endoscopic anchoring device can only deliver and deploy anchors from the device itself, from the point of entry in the abdomen. Although it is now currently used in laparoscopic surgery, there would be no incentive to do so as either one less laparoscopic port would be available for other tools or one more laparoscopic port would be necessary.

Although not desirable, adding one extra laparoscopic port is however sometimes required since no alternatives currently exists. For example, to retract solid organs such as liver, specific dedicated retracting tools are used. Using the additional laparoscopic port nevertheless defeats the purpose of the laparoscopic surgery, which is to use as few ports and be as little intrusive as possible.

The devices discussed above display noticeable shortcomings in that they either may not be anchored adequately inside the abdominal cavity, use a laparoscopic port that could otherwise be used for other purposes, or do not allow multiple organs to be retracted in a time efficient manner. There is therefore a clear need for a better retracting tool adapted to laparoscopic surgery.

SUMMARY OF THE INVENTION

It is an object of the present invention to provide a laparoscopic tool that decreases the amount of time necessary to retract an organ.

It is another object of the present invention to provide a laparoscopic tool that leaves a laparoscopic port free for other tools to be inserted while performing its retracting function.

It is a further object of the present invention to provide a laparoscopic tool that provides more flexibility for changing a position from which a retraction is made than known laparoscopic tools or methods.

In a first embodiment there is disclosed a laparoscopic tool for surgery on an internal body tissue of a patient. The laparoscopic tool comprises a main body to which is affixed an attachment. The main body has a main aperture for fixing a compatible anchor. The attachment has a support member, which is connected to the main body, and a needle portion itself connected to the support member. The needle portion has an interlocking mechanism to interlock with the support member. The attachment is deployable from a first position aligned with the main body, for insertion through a laparoscopic port, to a second position unaligned with the main body, for insertion into a tissue and for anchoring the tool to the tissue.

In another embodiment, there is disclosed a method of performing a laparoscopic surgery on a first internal body tissue of a patient. The method of performing the laparoscopic surgery comprises inserting a laparoscopic tool through a laparoscopic port inserted into the body of a patient, securing the laparoscopic tool to a first internal body tissue of the patient and leaving the laparoscopic tool therein, attaching a first portion of a compatible anchor to the laparoscopic tool, and finally attaching a second portion of the compatible anchor to a second internal tissue of the patient.

In yet another embodiment, there is disclosed a use of a laparoscopic tool for surgery on an internal body tissue of a patient. The laparoscopic tool comprises a main body to which is affixed an attachment. The main body has a main aperture for fixing a compatible anchor and an attachment. The attachment has a support member which is connected to the main body, and a needle portion itself connected to the support member. The needle portion has an interlocking mechanism to interlock with the support member. The attachment is deployable from a first position aligned with the main body, for insertion through a laparoscopic port, to a second position unaligned with the main body, for insertion into a tissue and for anchoring the tool to the tissue.

In yet another embodiment, there is disclosed a kit for surgery on an internal body tissue of a patient. The kit comprises a laparoscopic tool and a compatible anchor. The laparoscopic tool comprises a main body to which is affixed an attachment. The main body has a main aperture for fixing a compatible anchor and an attachment. The attachment has a support member which is connected to the main body, and a needle portion itself connected to the support member. The needle portion has an interlocking mechanism to interlock with the support member. The attachment is deployable from a first position aligned with the main body, for insertion through a laparoscopic port, to a second position unaligned with the main body, for insertion into a tissue and for anchoring the tool to the tissue.

Other features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION OF THE PREFERRED EMBODIMENTS

The laparoscopic tool of the present invention is used to retract an organ during laparoscopic surgery by attaching the tool to a first internal body tissue, such as an inside wall of an abdominal cavity, and by attaching a compatible anchor between a target tissue, such as the organ, at one end, and the laparoscopic tool at the other end.

Figure 1:
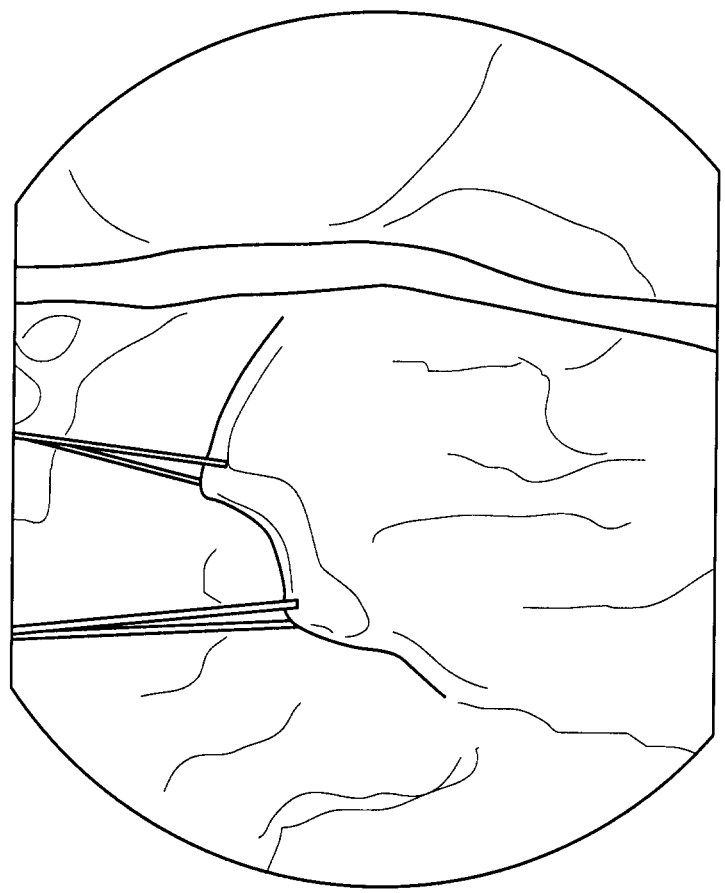
FIG. 1 is a perspective view of an abdominal cavity showing an organ being retracted by stitches passing through an abdominal wall as per a prior art method.
Figure 2:
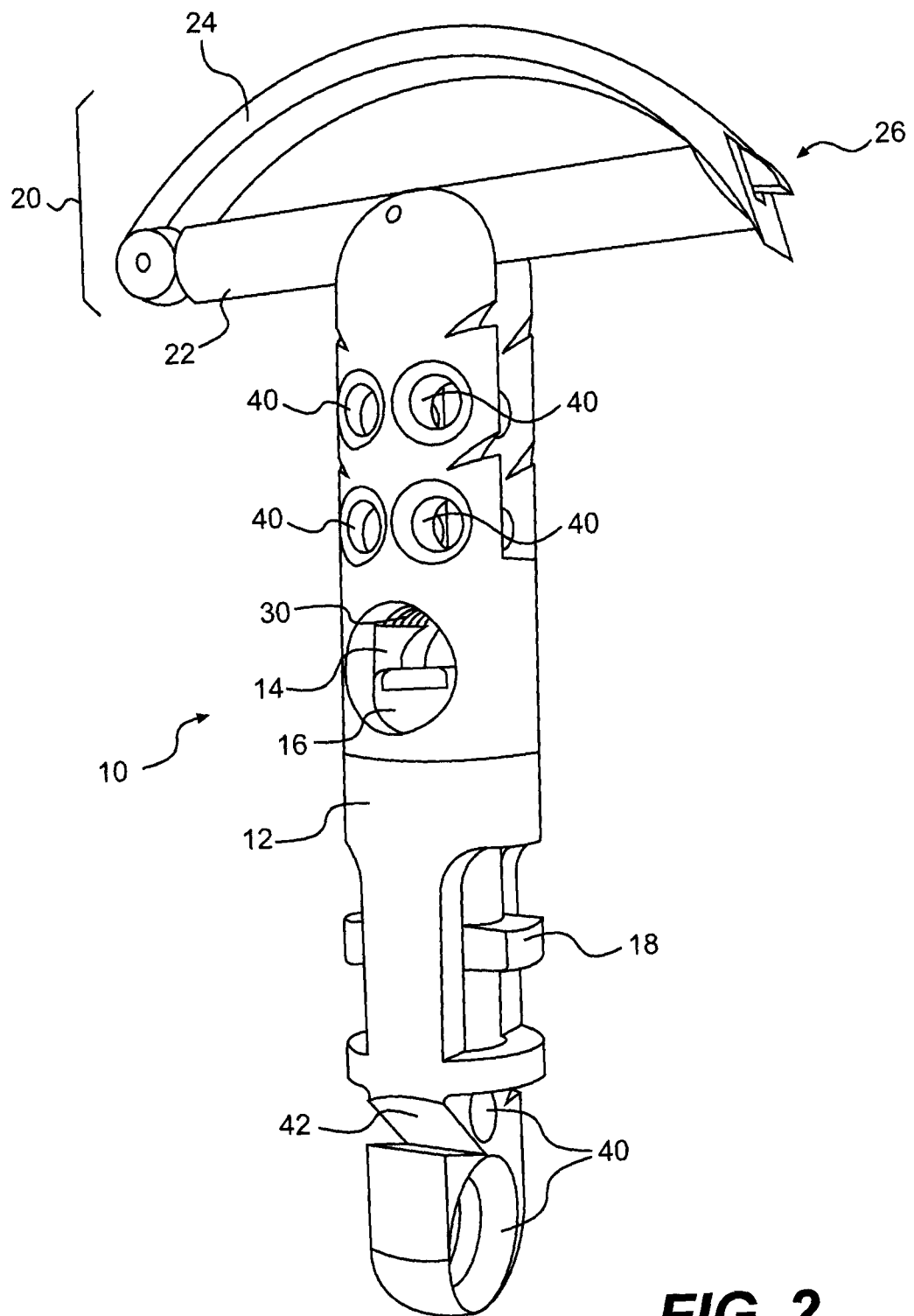
FIG. 2 is a perspective view of the laparoscopic tool having the support member and the needle portion interlocked in accordance with an embodiment of the present invention.

FIG. 2 shows the laparoscopic tool 10 in accordance with an embodiment of the present invention. The laparoscopic tool 10 comprises a main body 12 having a main aperture 14, adapted to receive a compatible anchor, and an attachment 20. The attachment 20 has a support member 22 connected to the main body 12, and a needle portion 24 connected to the support member 22. The needle portion 24 has an interlocking mechanism 26 to interlock with the support member 22. The support member 22 may be connected proximate its mid portion to the main body 12.

Figure 3:
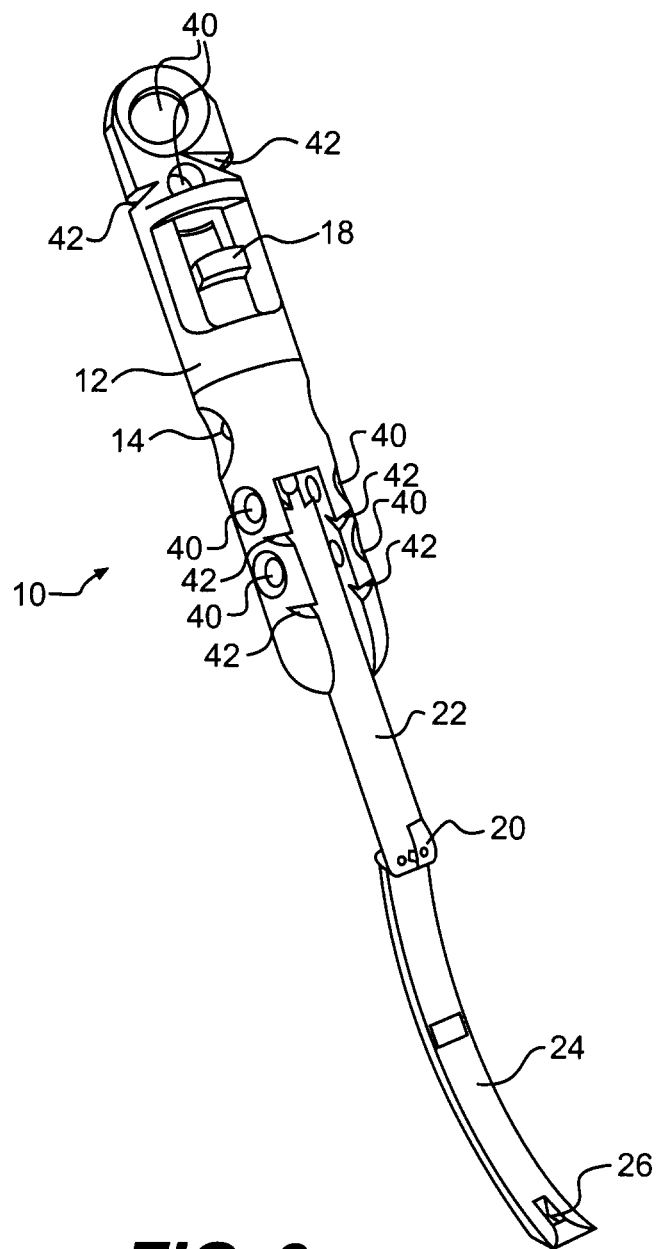
FIG. 3 is a perspective view of the laparoscopic tool of FIG. 2 having the support member and the needle portion deployed and aligned with the main body such as for insertion through a laparoscopic port.

FIG. 3 is now concurrently referred to. The attachment 20 is deployable from a deployed position aligned with the main body 12, as shown in FIG. 3, used for insertion into an abdominal cavity through a laparoscopic port, to a locking position unaligned with the main body 12, as shown in FIG. 2, for insertion into the internal body tissue and for securing the laparoscopic tool 10 to the tissue. Although shown as arcuate, the needle portion 24 may take different functional shapes. The cross-section of the needle portion is advantageously flattened so as to distribute the load of a retracted organ on a larger area of the internal body tissue in which the needle portion 24 is inserted. The needle portion 24 and the support member 22 may be made of a single flexible piece, or can be made of two separate pieces, as depicted, that are hingedly connected.

Figure 4:
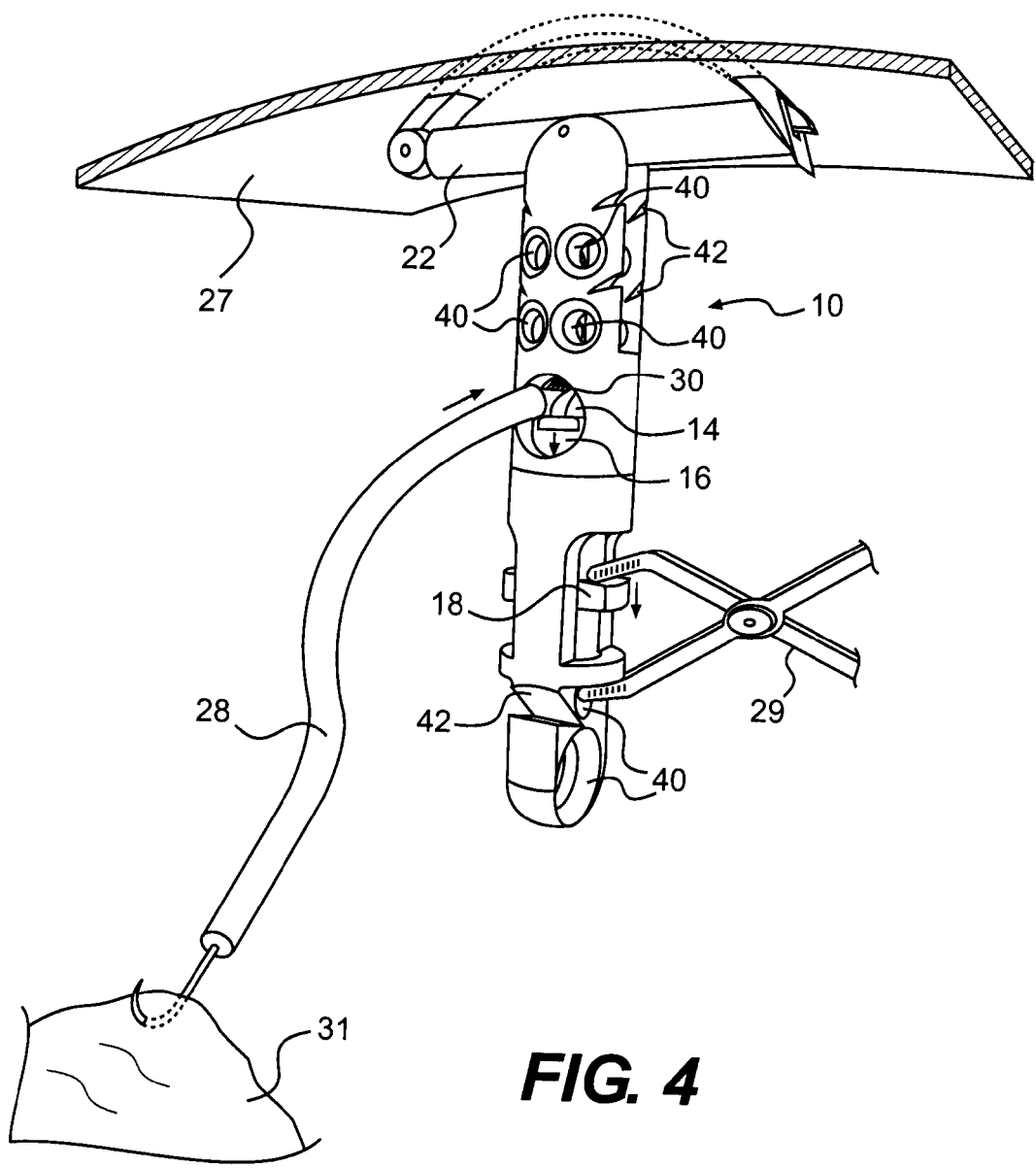
FIG. 4 is a perspective view of the laparoscopic tool of FIG. 2 inside an abdominal cavity showing the laparoscopic tool anchored in an abdominal wall and a compatible anchor attached to an organ to be retracted.

FIG. 4 is now concurrently referred to. The laparoscopic tool 10 is shown with its needle portion 24 inserted in the abdominal wall 27 (partially shown) and locked to the support member 22. An embodiment of a compatible anchor 28 is also shown. In one embodiment of the present invention, the main aperture 14 of the laparoscopic tool 10 comprises a locking mechanism 16. The locking mechanism 16 is releasable and is preferably biased closed so as to lock on the compatible anchor 28. The locking mechanism 16 comprises an actuating portion 18 to actuate the locking mechanism 16. This actuating portion 18 may be grabbed with another laparoscopic tool, such as a laparoscopic grasper 29 so as to open the main aperture 14 such that one end of the compatible anchor 28 may be inserted. One end of the compatible anchor may be inserted in the opened main aperture 14 after actuation of the locking mechanism 16, and the other end of the compatible anchor 28 may be attached to the target tissue, or organ 31.

The main aperture 14 of the laparoscopic tool 10 may comprise corrugations 30 therein. The corrugations 30 on the inside surface of the main aperture 14 provide added grip on the compatible anchor 28 once inserted in the main aperture 14. This prevents accidental removal of the compatible anchor 28.

To provide more attachment options, for example, to retract more than one organ, the laparoscopic tool 10 may comprise one or more secondary apertures 40 on the main body 12. Optionally, the secondary apertures 40 may also be equipped with one locking mechanism similar to the locking mechanism 16. Secondary apertures may be used to fix additional compatible anchors or to receive suture threads.

Optionally, the laparoscopic tool 10 may comprise one or more notches 42 on the main body 12. These notches 42 may be used to engage and hold in place suture threads, or thread-like portions of any compatible anchor used.

Figure 5B:
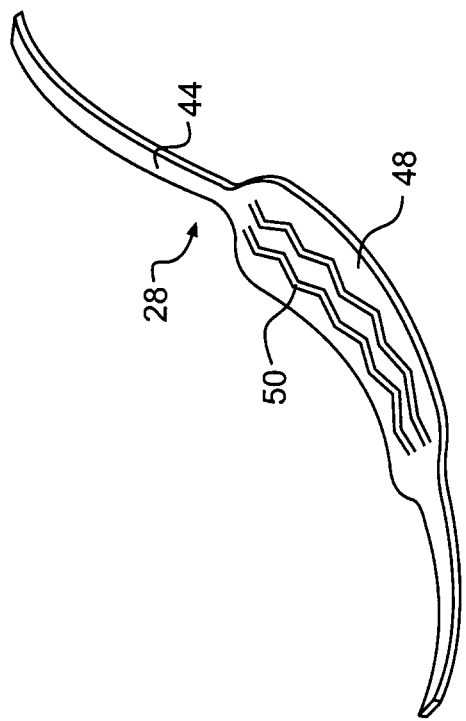
FIG. 5b is a perspective view of a type of compatible anchor having a widened support portion for use with the laparoscopic tool of FIG. 2 in accordance with another embodiment of the present invention.
Figure 5A:
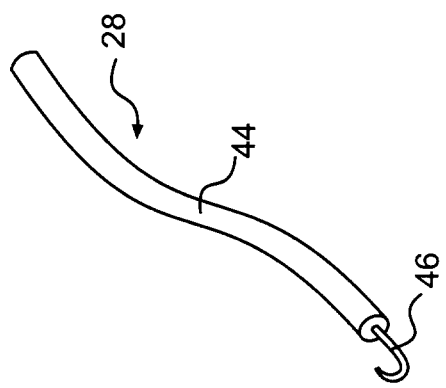
FIG. 5a is a perspective view of a sharp hook type of compatible anchor for use with the laparoscopic tool of FIG. 2 in accordance with an embodiment of the present invention.

FIGS. 5a to 5d, now referred to, show four different embodiments of the compatible anchor 28. As shown, the compatible anchor 28 may adopt different designs. For example, the compatible anchor 28 may comprise a resilient body 44, such as an elastic band, (of a material compatible with the human body) having a sharp hook 46 at one end to attach to the organ to be retracted. This embodiment is depicted in FIG. 5a. Alternatively, the compatible anchor 28 may comprise many resilient bodies 44, each having one sharp hook 46 at their respective end to attach to the one or to many organs to be retracted.

Alternatively, the compatible anchor 28 may have its resilient body 44 widened to provide a support portion 48, as shown in FIG. 5b. This widened support portion 48 may optionally comprise corrugations 50 or bosses (not shown), which prevent slipping of the retracted organ 31.

Figure 5D:
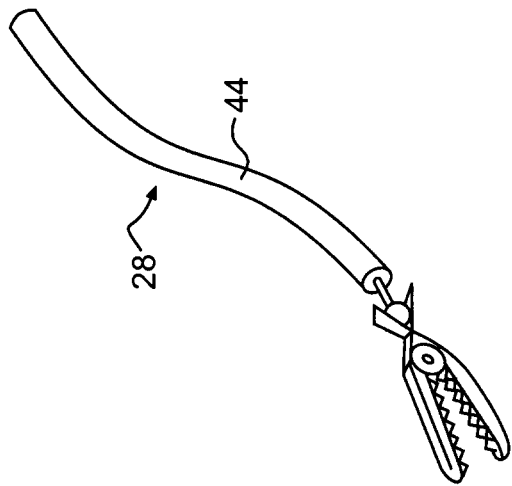
FIG. 5d is a perspective view of a grasper type of compatible anchor for use with the laparoscopic tool of FIG. 2 in accordance with another embodiment of the present invention.
Figure 5C:
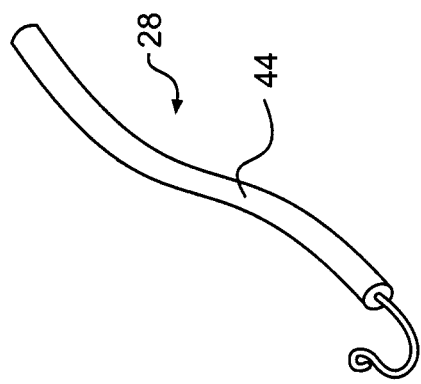
FIG. 5c is a perspective view of a blunt hook type of compatible anchor for use with the laparoscopic tool of FIG. 2 in accordance with another embodiment of the present invention.

FIG. 5c shows another embodiment of the compatible anchor 28. This type of compatible anchor is called a blunt hook type and is used to retract tubular structures, such as arteries.

FIG. 5d shows yet another embodiment of the compatible anchor 28, in this case, a grasper type. The grasper type is used to grasp tissues.

Figure 6:
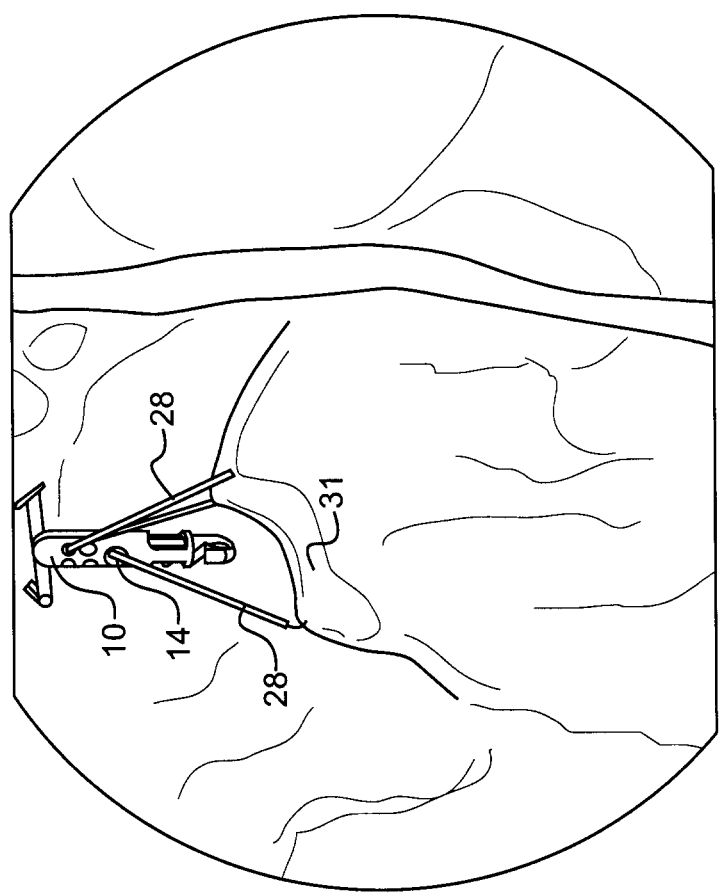
FIG. 6 is a perspective view of an abdominal cavity showing an organ being retracted by the laparoscopic tool of FIG. 2 with the compatible anchor of FIG. 5a, where the laparoscopic tool is attached to the abdominal wall and the compatible anchor is attached to the retracted organ.

FIG. 6 is now concurrently referred to. To proceed with a retraction of the organ, a first portion of the compatible anchor 28 is attached to the laparoscopic tool 10 by inserting it in the aperture 14. A second portion of the compatible anchor 28 is attached to the organ 31 to be retracted, and the compatible anchor 28 retracts the target organ by returning to its original shape by nature of its resiliency.

Figure 7:
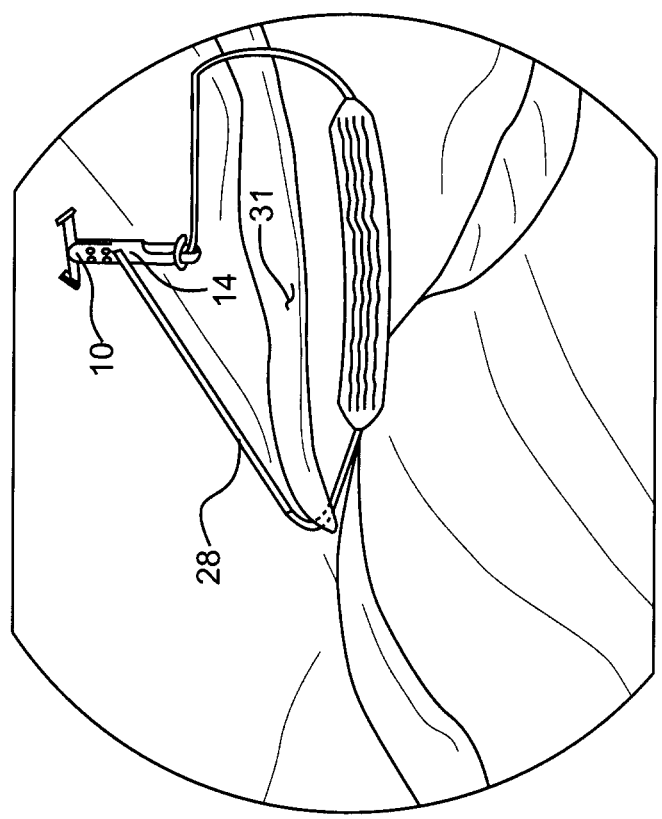
FIG. 7 is a perspective view of an abdominal cavity showing an organ being retracted by the laparoscopic tool of FIG. 2 with the compatible anchor of FIG. 5b, where the laparoscopic tool is attached to the abdominal wall and the compatible anchor is slipped under the retracted organ, in the present case a liver.

FIG. 7 is now concurrently referred to. To proceed with the retraction of the organ 31, the first portion of the compatible anchor 28 is attached to the laparoscopic tool 10 by inserting it in aperture 14. The compatible anchor 28 is slipped under the organ 31 to be retracted, thereby positioning the widened support portion 48 under the organ 31. The second portion of the compatible anchor 28 is attached to the laparoscopic tool 10 by inserting it into one of the secondary apertures 40. Following this, the compatible anchor 28 may be pulled through the aperture 14 to retract the target organ 31.

Alternatively, the compatible anchor 28 may be a thread-like material similar to threads used for stitching. In this case, the compatible anchor 28 is similar to the compatible anchor 28 depicted in FIG. 5a except that the body 44 is not resilient, but takes the form of a thread, such as a suture thread. To proceed with a retraction of the organ 31, a first portion of the compatible anchor 28 is attached to the laparoscopic tool 10 by inserting it in aperture 14. The compatible anchor 28 may be pushed through the target organ 31 with the hook 46. Otherwise, the compatible anchor 28 may be wound around the target organ 31 to be retracted and the second portion of the compatible anchor 28 may be attached to the laparoscopic tool 10 by inserting it into one of the secondary apertures 40. The organ 31 is retracted by pulling on the compatible anchor 28 or by any other manner available within the confined space of the abdomen.

In the preceding examples, reference was made to a target tissue that is usually different than the tissue where the laparoscopic tools 10 has been inserted. However, it would alternatively be possible to attach the compatible anchor 28 to the same tissue as the tissue where the laparoscopic tool 10 was inserted so that the tissue is retracted on itself. In use, a surgeon performs the laparoscopic surgery on the patient by inserting the laparoscopic tool 10 through the laparoscopic port in the abdomen of the patient. The attachment 20 of the laparoscopic tool 10 must be in its aligned position, displayed at FIG. 3, for being inserted in the laparoscopic port. Using the suitable handling tool inserted in a second laparoscopic port, the surgeon then secures the laparoscopic tool 10 to the wall of the internal abdominal cavity of the patient. The laparoscopic tool 10 being secured, the surgeon may then reuse the laparoscopic port in which the laparoscopic tool 10 was inserted for insertion of other tools or devices. To proceed with a retraction of one organ, the first portion of the compatible anchor 28 is attached to the laparoscopic tool 10, and the second portion of the compatible anchor 28 is attached to the organ 31 to be retracted. Alternatively, the compatible 28 may be slipped under, pushed through, or wound around the target organ 31 before the second portion of the compatible anchor 28 is inserted into one of the secondary apertures 40 and the organ is retracted by a pulling action applied to the compatible anchor 28.

In another embodiment of the invention, a kit is provided that may be sold ready for use by surgeons. The kit comprises the laparoscopic tool 10 in accordance with the present invention, along with suitable compatible anchors 28. The suitable compatible anchors 28 may be simple suture threads, or be of thread-like configurations, comprise resilient portions, hooks, support strips for the organs (with and without corrugation or bosses to provide resistance and prevent slippage).

The embodiments and examples presented herein are illustrative of the general nature of the subject matter claimed and are not limiting. It will be understood by those skilled in the art how these embodiments can be readily modified and/or adapted for various applications and in various ways without departing from the spirit and scope of the subject matter disclosed claimed. The claims hereof are to be understood to include without limitation all alternative embodiments and equivalents of the subject matter hereof. Phrases, words and terms employed herein are illustrative and are not limiting. Where permissible by law, all references cited herein are incorporated by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed.

The invention claimed is:

1. A laparoscopic tool for use with a compatible anchor in surgery on an internal body tissue of a patient, said laparoscopic tool comprising:
   a main body having a main aperture for fixing a compatible anchor; and an attachment having
   a support member connected to said main body; and
   a needle portion connected to said support member, said needle portion having an interlocking mechanism to interlock with said support member, and said needle portion being pivotally connected to said support member,
   wherein said attachment is deployable from a first position aligned with said main body, for insertion into a laparoscopic port, to a second position unaligned with said main body, for insertion into a tissue and for anchoring said tool to said tissue.

2. The laparoscopic tool of claim 1, wherein said main aperture is corrugated therein.

3. The laparoscopic tool of claim 1, wherein said main body further comprises at least one notch.

4. The laparoscopic tool of claim 1, wherein said needle portion is arcuate.

5. The laparoscopic tool of claim 1 wherein said needle portion has a flat cross-section.

6. The laparoscopic tool of claim 1, wherein said support member is pivotally connected to said main body.

7. The laparoscopic tool of claim 1, wherein said main body is connected proximate a mid portion of said support member.

8. The laparoscopic tool of claim 1, wherein said main aperture further comprises a first locking mechanism.

9. The laparoscopic tool of claim 8, further comprising an actuating portion to actuate said first locking mechanism, said first locking mechanism being normally biased closed and releasable with said actuating portion.

10. The laparoscopic tool of claim 1, wherein said main body further comprises at least one secondary aperture.

11. The laparoscopic tool of claim 10, wherein said at least one secondary aperture further comprises a second locking mechanism.

12. A kit for surgery on an internal body tissue of a patient, said kit comprising:
a laparoscopic tool as claimed in claim 1, and
a compatible anchor, adapted to be inserted in said main aperture.

13. A method of performing laparoscopic surgery on an internal body tissue of a patient comprising:
inserting a laparoscopic tool as claimed in claim 1, through a laparoscopic port inserted into a body of the patient;
securing said laparoscopic tool to a first internal body tissue of the patient and leaving said laparoscopic tool therein;
attaching a first portion of a compatible anchor to said laparoscopic tool; and
functionally placing a second portion of said compatible anchor in contact with a second internal tissue of the patient so as to retract said second internal tissue.

14. The method of claim 13, wherein said placing comprises inserting a hook of said compatible anchor in said second internal tissue.

15. The method of claim 13, wherein said placing comprises winding a thread around said second internal tissue.

16. The method of claim 13, wherein said placing comprises placing said compatible anchor under said second internal tissue and attaching a second portion of said compatible anchor to said laparoscopic tool.

17. The method of claim 13, wherein said second internal tissue is said first internal tissue.

18. The method of claim 13, further comprising retracting said second internal tissue.

19. The method of claim 18, wherein said retracting comprises pulling on said compatible anchor.

* * * * *